(12) United States Patent
Nathan

(10) Patent No.: US 9,817,131 B2
(45) Date of Patent: Nov. 14, 2017

(54) MOVING PET GANTRY

(71) Applicant: General Electric Company, Schenectady, NY (US)

(72) Inventor: Adam Clark Nathan, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 14/584,383

(22) Filed: Dec. 29, 2014

(65) Prior Publication Data

US 2016/0183890 A1   Jun. 30, 2016

(51) Int. Cl.
*G01T 1/16* (2006.01)
*A61B 6/03* (2006.01)
(Continued)

(52) U.S. Cl.
CPC .......... *G01T 1/1615* (2013.01); *A61B 6/4275* (2013.01); *A61B 6/4411* (2013.01);
(Continued)

(58) Field of Classification Search
CPC .. A61B 6/00; A61B 6/03; A61B 6/035; A61B 6/037; A61B 6/42; A61B 6/4266; A61B 6/4275; A61B 6/44; A61B 6/4411; A61B 6/4417; A61B 6/4429; A61B 6/4435; A61B 6/4447; A61B 6/58; A61B 6/589; A61B 2050/105; A61B 50/10; A61B 2562/16; A61B 2560/00; A61B 2560/02; A61B 2560/04; A61B 2560/0406; A61B 2560/0443; A61B 2560/06; A61B 2576/00; G01T 1/00; G01T 1/16; G01T 1/1603; G01T 1/161; G01T 1/1615; G01T 1/163; G01T 1/1635; G01T 1/29; G01T 1/2964; G01T 1/2971; G01T 1/2985; G01T 7/00; G01N 23/00; G01N 23/08; G01N 23/22; G01N 23/2206; G01N 2223/00; G01N 2223/03; G01N 2223/045; G01N 2223/07;
(Continued)

(56) References Cited

U.S. PATENT DOCUMENTS 7,162,004 B2   1/2007  Inoue et al.
7,991,115 B2 * 8/2011  Matsuzawa ............ A61B 6/032
                                                    250/394
(Continued)

FOREIGN PATENT DOCUMENTS

CN           1537514 A      10/2004

OTHER PUBLICATIONS

Unofficial English translation of Chinese Office Action issued in connection with corresponding CN Application No. 201521109617.3 dated May 3, 2016.

*Primary Examiner* — Anastasia Midkiff
(74) *Attorney, Agent, or Firm* — Dean D. Small; The Small Patent Law Group, LLC

(57) ABSTRACT

An apparatus is described herein. The apparatus comprises a first modality unit and a second modality unit. The first modality unit is located within a gantry. The second modality unit within the gantry is moveable along an examination axis to be concentric about with the first modality unit such that a field of view of the first modality unit and a field of view of the second modality unit are centered about a single point of interest.

20 Claims, 3 Drawing Sheets

(51) Int. Cl.
*G01T 1/161* (2006.01)
*A61B 6/00* (2006.01)

(52) U.S. Cl.
CPC ............ *A61B 6/4417* (2013.01); *A61B 6/032* (2013.01); *A61B 6/037* (2013.01); *A61B 2560/0443* (2013.01); *G01N 2223/045* (2013.01)

(58) Field of Classification Search
CPC ......... G01N 2223/071; G01N 2223/31; G01N 2223/308; G01N 2223/32; G01N 2223/321; G01N 2223/3303; G01N 2223/40; G01N 2223/419; G01N 2223/50; H05G 1/00; H05G 1/02; H01J 37/00; H01J 37/02; H01J 37/023; H01J 37/16; H01J 37/20; H01J 37/244; H01J 2237/00; H01J 2237/20; H01J 2237/244; H01J 2237/24415; H01J 2237/2448
See application file for complete search history.

(56) References Cited

U.S. PATENT DOCUMENTS

| | | | |
|---|---|---|---|
| 8,351,566 B2 | 1/2013 | Sawanaga | |
| 8,630,696 B2 | 1/2014 | Kim et al. | |
| 2003/0058984 A1* | 3/2003 | Susami | A61B 6/4417 378/19 |
| 2003/0212320 A1* | 11/2003 | Wilk | A61B 6/032 600/407 |
| 2004/0066909 A1 | 4/2004 | Lonn et al. | |
| 2005/0207530 A1* | 9/2005 | Inoue | A61B 6/032 378/63 |
| 2008/0001089 A1* | 1/2008 | Lusser | G01T 1/249 250/363.02 |
| 2009/0213983 A1* | 8/2009 | Vaquero Lopez | A61B 6/032 378/4 |
| 2011/0288397 A1* | 11/2011 | Inoue | A61B 6/037 600/407 |
| 2013/0003918 A1* | 1/2013 | Takayama | A61B 6/032 378/19 |

* cited by examiner

100

300

MOVING PET GANTRY

BACKGROUND OF THE INVENTION

Various technologies exist wherein portions of a patient are imaged to study tissues or organs within the body. For example, nuclear medicine includes techniques where a radiopharmaceutical is introduced to a patient that causes the emission of photons from the body of the patient. The radiopharmaceutical concentrates in particular tissues of the body, indicating tissue metabolic activity at the site of concentration and emitting a higher amount of photons from the site of concentration. Images may be reconstructed from photons observed during Positron Emission Tomography (PET) scan. PET scans may be combined with computerized tomography (CT) scans to develop an image of tissues and organs of a patient.

During a scan, a patient support surface moves as necessary between the CT and the PET fields of view (FoV) to obtain PET scans and CT scans of the patient's anatomy. During movement of the patient to obtain PET scans and CT scans differences in deflection of the patient on the patient support surface may occur. This results in a higher chance for error in the resulting images.

SUMMARY OF THE INVENTION

An embodiment relates to an apparatus. An apparatus comprises a first modality unit and a second modality unit. The first modality unit is located within a gantry. The second modality unit within the gantry is moveable along an examination axis to be concentric about with the first modality unit such that a field of view of the first modality unit and a field of view of the second modality unit are centered about a single point of interest.

Another embodiment relates to a system. The system comprises a patient support surface and a gantry. The patient support surface is to support a patient during an imaging procedure. The gantry includes a Computed Tomography (CT) modality unit and a Positron Emission Tomography (PET) modality unit, wherein the CT modality unit is positioned about a bore of the gantry and the PET modality unit is moveable along an examination axis to be concentric with the bore of the gantry.

Still another embodiment relates to a method. The method comprises attaching a plurality of PET detector units to a ring structure and movably positioning the ring structure within a gantry. The method also comprises positioning a Computed Tomography (CT) modality unit rotatably about an examination axis.

BRIEF DESCRIPTION OF THE DRAWINGS

The present techniques will become more fully understood from the following detailed description, taken in conjunction with the accompanying drawings, wherein like reference numerals refer to like parts, in which.

In some cases, the same numbers are used throughout the disclosure and the figures to reference like components and features. Numbers in the 100 series refer to features originally found in FIG. 1; numbers in the 200 series refer to features originally found in FIG. 2; and so on.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As discussed above, imaging systems may include a plurality of modality units, such as PET and CT scanners. In the embodiments discussed herein, a moveable PET gantry obtains PET scans. A technical effect of at least one embodiment includes a mechanism for moving a PET modality unit within a bore of a gantry, wherein CT modality unit is to rotate about the bore, resulting in a smaller imaging system footprint. In some scenarios, the CT-to-PET image registration is improved. In particular, the center of the PET FoV is physically aligned with the center of the CT FoV, resulting in less error between the CT FoV and the PET FoV.

Figure 1:
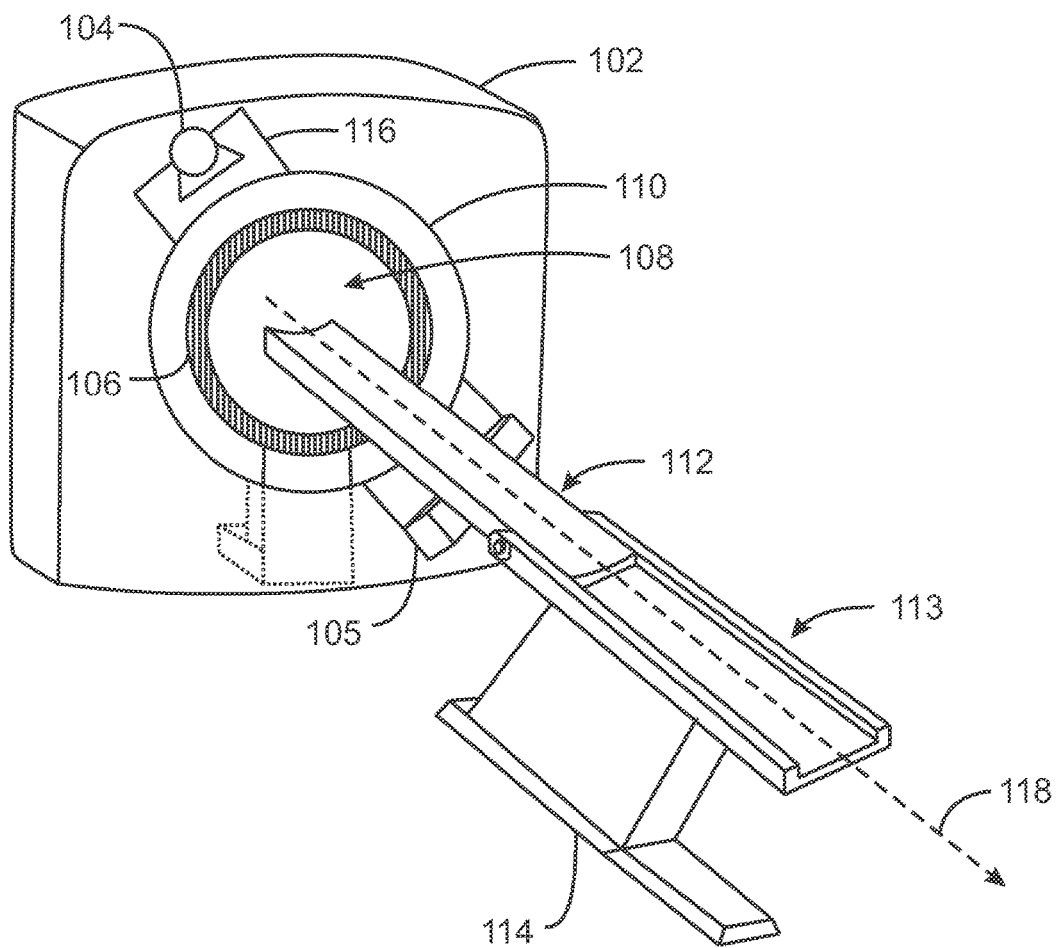
FIG. 1 is an illustration of a multi-modality imaging system.

FIG. 1 is a perspective view of an exemplary medical imaging system 100. The imaging system 100 is a multi-modality imaging system that includes both a Positron Emission Tomography (PET) modality unit and a Computed Tomography (CT) modality unit. Although the present techniques are described using particular modality units, any modality unit may be used. For example, the imaging system 100 may include one or more types of imaging modality units, such as a Single Photon Emission Computed Tomography (SPECT) modality unit, an ultrasound modality unit, a Magnetic Resonance Imaging (MRI) modality unit, an X-radiation (X-ray) radiography or fluoroscopy modality unit, and/or any other modality unit capable of generating images of a region of interest (ROI) of a patient. The images at the ROI are obtained in widths equal to the width of the FoV. The various embodiments are not limited to medical imaging systems for imaging human subjects, but may include, for example, veterinary systems. As used herein, the term "patient" may refer to a human patient or any other animal.

Referring to FIG. 1, the multi-modality imaging system 100 includes gantry 102 with a CT modality unit 104 and a PET modality unit 106. A field of view (FoV) 108 is located within the bore 110 of the gantry 102. In embodiments, the FoV may originate at the CT modality unit 104 or the PET modality unit 106, depending on the type of scan being performed. A cradle 112 is positioned atop of a table structure 113. The cradle may be extended from the table structure 113 to position a patient within the bore 110 via a motorized pedestal 114. The cradle 112, table structure 113, and pedestal 114 form a patient support surface. The pedestal 114 enables the cradle 112 to extend into the bore 110 from the table structure 113 to properly position the patient within the FoV during a medical imaging procedure. Although the patient support surface is described with particular components, the patient support surface may include fewer or more components than the components described herein.

The gantry 102 includes a rotor 116 that supports the CT modality unit 104. The CT modality unit 104 includes a detector array 105 and may acquire X-ray attenuation data at a variety of views around a patient located on the cradle 112. In FIG. 1 the CT modality 104 unit may be a source of X-rays. In embodiments, the X-ray source may be an X-ray tube, a distributed X-ray source, or any other source of X-rays for the purpose of medical imaging. The views are obtained by rotating the CT modality unit 104 and a detector array 105 about the bore 110 using the rotor 116. The rotor 116 may be configured to rotate the CT modality unit about a longitudinal or examination axis 118 that may extend through a bore 110 of the multi-modality imaging system 100. The bore 110 extends through the gantry 102 along the longitudinal axis 118. The bore 106 is sized and shaped to allow a patient (not shown) to be moved into and out of the bore 106.

After or prior to the CT scan, a PET structure 106 can be moved within the bore 110 to complete a PET scan. During a PET scan, a radiopharmaceutical is introduced to a patient. The radiopharmaceutical then causes the emission of photons from the body of the patient. The radiopharmaceutical may concentrate in particular tissues of the body, indicating tissue metabolic activity at the site of concentration and emitting a higher amount of photons from the site of concentration. Images may be reconstructed from photons observed by detectors within the PET ring structure, such as the PET modality unit 106. The ring structure may include a plurality of PET detectors, configured to observe the photons that occur in a coincident event as emitted from a patient that has been introduced to a radiopharmaceutical. In embodiments, the PET ring structure described herein is a full ring structure.

The pedestal 114 is configured to selectively move the cradle 112 along the longitudinal axis 118 into and out of the bore 110. The PET modality unit 106 is also configured to selectively move the cradle 112 along the longitudinal axis 118 into and out of the bore 110. Since the PET modality unit 106 can also move within the bore 110, the patient may be subjected to less movement. For example, a medical imaging procedure may include first positioning a patient on the cradle 112 while the cradle 112 is positioned atop of the table structure on the motorize pedestal 114. The cradle 112 is located outside of the bore 110 of the gantry 102 when the patient is loaded onto the cradle 112. With the patient in position, the pedestal 114 may cause the cradle 112 to extend from atop the table structure 113 into the bore 110. A PET modality unit 106 may then extend into the area of the bore 110 in which the CT modality unit 104 is located and obtain PET images from the patient. Moving the PET detector inside the CT gantry greatly reduces the amount of cradle extension needed to reach the PET FoV, resulting in a reduction of gross and differential deflection in PET FoV. In some scenarios, when PET images are obtained from multiple fields of view. The PET modality unit may then retract from the area of the bore 110 in which the CT modality unit 104 is located, and the CT modality unit 104, including the detector array 105, may rotate around the bore 110 by operation of the rotor 116 to obtain CT images of the patient. Although the PET scan was described as occurring prior to the CT scan in the present example, the various scans from a multi-modality unit can occur in any order, and are not limited to the particular sequences described herein.

In the present techniques, the CT and PET systems are combined into a single gantry. This results in a smaller system footprint since a single gantry is used. Moreover, the size of the room housing the medical imaging system is smaller due to the smaller gantry. Additionally, the system footprint and the room housing the system is reduced in size because the cradle does not need space to travel between the CT and PET fields of view since the PET modality unit travels in and out of the bore. The present techniques also result in a simpler, smaller, less expensive table since the table does not need travel and/or an additional motion axis to move between CT and PET fields of view. In embodiments, the table used in the multi-modality system described herein may be the same as a table for use with just a CT modality unit, resulting in lower costs and higher volume as one table can be manufactured for a variety of systems.

Figure 2A:
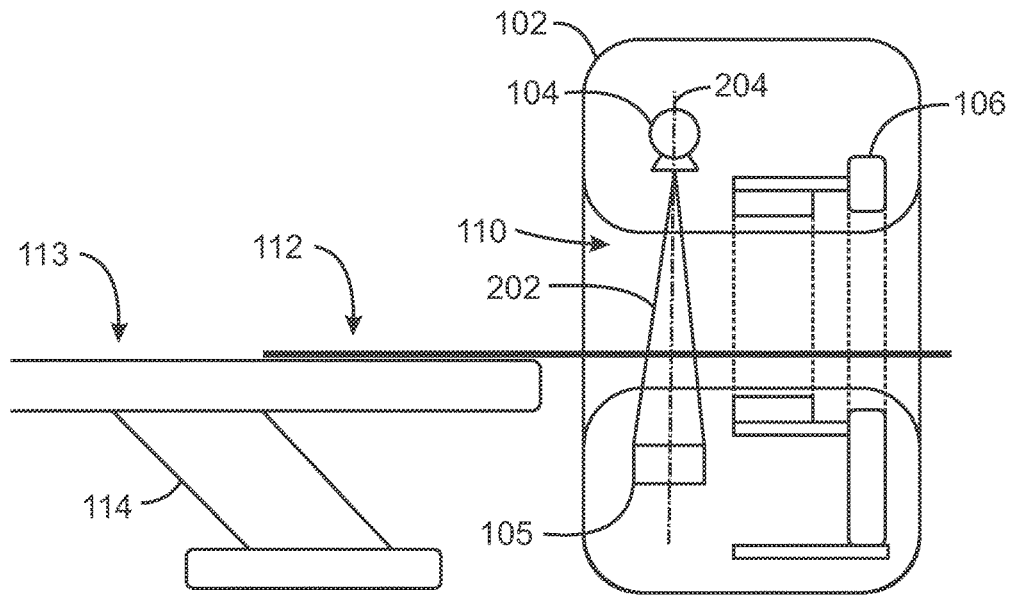
FIG. 2A is an illustration of the cross-section of a multi-modal imaging system configured for a first imaging procedure.

FIG. 2A is an illustration of the cross-section of a multi-modal imaging system 200A configured for a first imaging procedure. In embodiments, the first imaging procedure is a CT scan performed by a CT modality unit 104. The multi-modality imaging system 200A includes a gantry 102 with a CT modality unit 104 and a PET modality unit 106. A cradle 112 may position a patient within the bore 110 via a motorized pedestal 114. As discussed above, the pedestal 114 enables the cradle 112 to extend into the bore 110 to properly position the patient within the FoV during a medical imaging procedure.

During a CT scan, a detector array 105 collects X-rays from the CT modality unit 104. The detector array 105 is centered about the CT scan plane 204. In particular, the CT modality unit may project a cone 202 of x-rays that are detected by the detector array 105. In particular, X-rays from the CT modality unit 104 are a cone-shaped beam that passes through the patient. A portion of the X-ray radiation can pass around the patient, and both X-rays that pass through and around the patient impacts the detector array 105. Detector elements of the array produce electrical signals that are acquired and processed to reconstruct images of the anatomy of the patient.

Figure 2B:
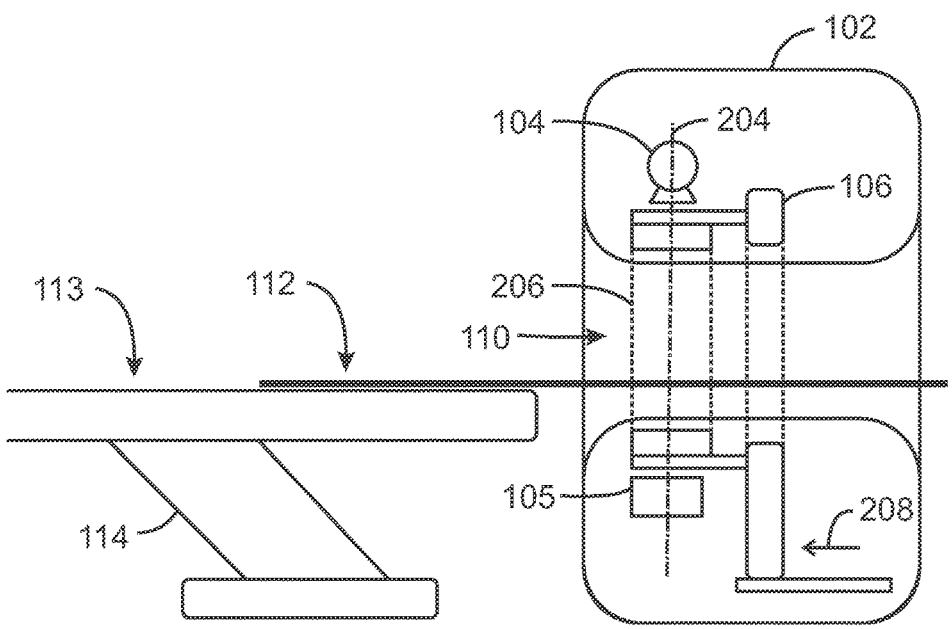
FIG. 2B is an illustration of the cross-section of a multi-modal imaging system configured for a second imaging procedure.

FIG. 2B is an illustration of the cross-section of a multi-modal imaging system 200B configured for a second imaging procedure. In embodiments, the second imaging procedure is a PET scan performed by the PET modality unit 106. The multi-modality imaging system 200A includes a gantry 102 with a CT modality unit 104 and a PET modality unit 106. A cradle 112 may position a patient within the bore 110 via a motorized pedestal 114. The PET modality unit 106 includes a full ring of detector units. In embodiments, the PET modality unit is mounted onto a full ring structure separate from the CT modality unit.

As illustrated, the PET modality unit 106 is positioned within the bore 110 to be concentric with the CT modality unit. In this manner, the center of the PET FoV 206 is physically aligned with the CT scan plane 204 such that the PET modality unit obtains PET images at the same location as the CT modality unit. In embodiments, the PET modality unit 106 is moved as indicated by arrow 208 along an examination axis that is parallel with the cradle 112.

The present techniques result in an improved CT-to-PET image registration, since the center of the PET FoV is physically aligned with the center of the CT FoV. Traditionally, due to deflection of the table, the patient anatomy is at a different height during the final PET can than where that same anatomy was during the CT scan. Moving the PET system so that it is aligned with the CT system greatly reduces this potential error. Moreover, the present techniques result in improved PET-to-PET bed registration because the table structure is closer to the PET field of view during PET imaging. Traditionally, the PET FoV was located behind the CT FoV, resulting in the need to the cradle to extend much further from the table support to obtain PET images when compared to the cradle position used during CT imaging.

In embodiments, a first modality unit of the gantry is stationary in a direction along the longitudinal axis. However, the first modality unit can rotate about the longitudinal axis. A second modality unit within the gantry is to be moveable along the examination axis, and may or may not rotate about the examination axis. When the second modality unit is outside of the area of a bore of the gantry in which the first modality unit is located, the second modality unit is in a retracted state. When the second modality unit is positioned within the area of a bore of the gantry in which the first modality unit is located, it is in a deployed state. A medical imaging procedure using the second modality unit can be performed when the second modality unit is in a deployed or retracted state.

Figure 3:
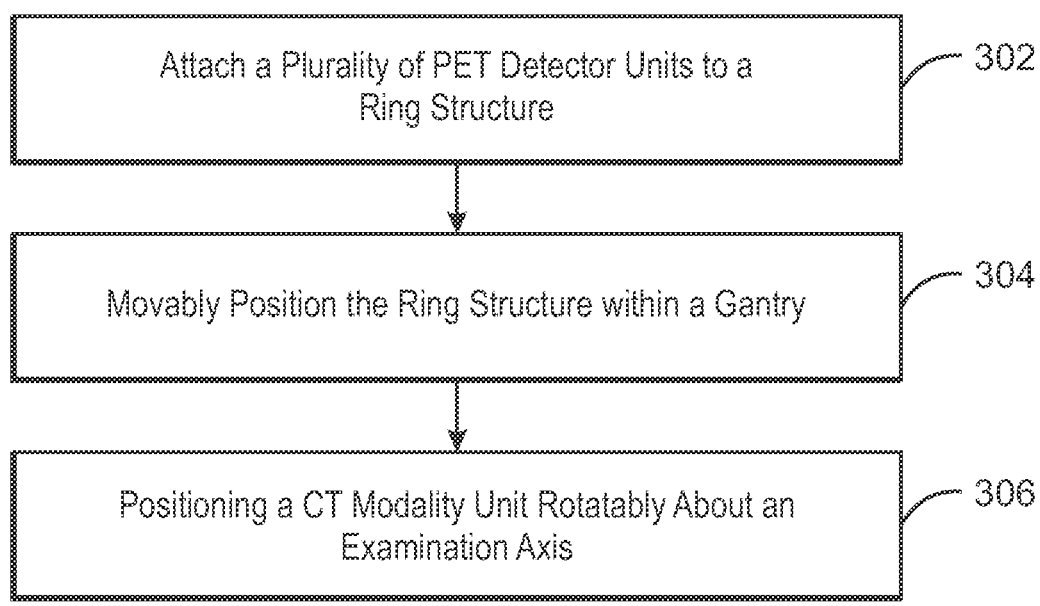
FIG. 3 is a process flow diagram of a method 300 for a moving PET gantry.

FIG. 3 is a process flow diagram of a method 300 for a moving PET gantry. At block 302, a plurality of PET detector units is attached to a ring structure. The plurality of PET detector units are to form a full ring of detector units about the ring structure. At block 304, the ring structure is movably positioned within a gantry. In some cases, the PET modality unit is located outside of a bore of the gantry and is to move inside the bore of the gantry when the PET modality unit is used during an imaging procedure. In embodiments, the ring structure may be moved within a bore of the gantry along the examination axis to obtain the PET scan. At block 306, a Computed Tomography (CT) modality unit is positioned rotatably about an examination axis. The CT unit is to be rotated about the bore and the examination axis to obtain a CT scan at the same point of interest as the PET modality unit. In this manner, a CT modality unit and a PET modality unit can obtain images at the same point of interest.

In some cases, PET and CT gantries are physically placed next to each other with the CT gantry closer to the patient table. The table cradle is configured to move into the bore for the CT scan. After the CT scan is complete, the PET detector ring, which is mounted so that it is cantilevered off of a PET gantry structure towards the CT, is moved inside the bore of the CT gantry on a linear motion device. The PET detector ring is designed to fit between the rotating envelope of the CT gantry and the inside bore cover. The PET gantry is moved until the center of the PET axial field of view aligns with the center of the CT axial field of view. The PET scan then commences using the same table axis of motion as was used during the CT scan.

While embodiments are described herein with respect to modality units used in the medical field, embodiments described herein can encompass those situations in which any modality unit is used in an imaging procedure. Further, those of skill in the art will recognize that the present techniques are applicable to many different hardware configurations, software architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus, comprising:
a first modality unit, wherein the first modality unit is located within a gantry, the first modality unit defining a scan plane passing through a detector of the first modality unit; and
a second modality unit within the gantry, the second modality unit defining a field of view (FOV), wherein the second modality unit is moveable along an examination axis such that the FOV of the second modality unit physically aligns with the scan plane of the first modality, and the FOV of the second modality unit and the scan plane of the first modality unit simultaneously physically overlap.

2. The apparatus of claim 1, wherein the first modality unit is a Computed Tomography (CT) modality unit.

3. The apparatus of claim 1, wherein the second modality unit is a Positron Emission Tomography (PET) modality unit.

4. The apparatus of claim 1, wherein the second modality unit is a Positron Emission Tomography (PET) modality unit with a full ring structure.

5. The apparatus of claim 1, wherein the second modality unit is moveable from a retracted position to an imaging position at which a center of the FOV of the second modality unit aligns with and overlaps a center of the scan plane of the first modality unit when the second modality unit is used for imaging.

6. The apparatus of claim 1, wherein the first modality unit is to rotate about a bore at the center of the gantry.

7. The apparatus of claim 1, wherein the first modality unit and the second modality unit are in parallel.

8. The apparatus of claim 1, wherein the first modality unit and the second modality unit are mounted to separate mounting structures within the gantry.

9. A system, comprising:
a patient support surface, wherein the patient support surface is to support a patient during an imaging procedure;
a gantry, wherein the gantry includes a Computed Tomography (CT) modality unit and a Positron Emission Tomography (PET) modality unit, the CT modality unit defining a scan plane passing through a detector of the CT modality unit and the PET modality unit defining a field of view (FOV), wherein the CT modality unit is positioned about a bore of the gantry and the PET modality unit is moveable along an examination axis such that the FOV of the PET modality unit physically aligns with the scan plane of the CT modality unit, and the FOV of the PET modality unit and the scan plane of the CT modality unit simultaneously physically overlap.

10. The system of claim 9, wherein the PET modality unit comprises a full ring of detectors.

11. The system of claim 9, wherein the PET modality unit is to be concentric with the bore of the gantry during a PET imaging procedure.

12. The system of claim 9, wherein the CT modality unit comprises an x-ray detector, wherein the x-ray detector is to rotate about the bore.

13. The system of claim 9, wherein the CT modality unit and the PET modality unit are mounted to separate mounting structures within the gantry.

14. The system of claim 9, wherein the CT modality unit and the PET modality unit are centered about a single point of interest.

15. The system of claim 9, wherein the CT modality unit is fixed along an examination axis, and rotatable about the examination axis.

16. A method, comprising:

attaching a plurality of PET detector units to a ring structure, the PET detector units defining a field of view (FOV);

movably positioning the ring structure within a gantry;

positioning a Computed Tomography (CT) modality unit defining a scan plane passing through a detector of the CT modality unit rotatably about an examination axis; and moving the PET detector units such that the FOV of the PET detector units physically aligns with the scan plane of the CT modality unit, and the FOV of the PET detector units and the scan plane of the CT modality unit simultaneously physically overlap.

17. The method of claim 16, wherein the plurality of PET detector units form a full ring of detector units about the ring structure.

18. The method of claim 16, comprising moving the ring structure within a bore of the gantry along the examination axis to obtain a PET scan.

19. The method of claim 16, comprising rotating the CT modality unit about the bore and the examination axis to obtain a CT scan.

20. The method of claim 16, wherein the ring structure is moved from a retracted position to an imaging position at which a center of the FOV of the PET detector units aligns with and overlaps a center of the scan plane of the CT modality unit when the PET detector units are used for imaging.

* * * * *